United States Patent [19]

McGhee et al.

[11] 4,114,605
[45] Sep. 19, 1978

[54] INTRAORAL CUP FOR COLLECTING SALIVA AND METHOD OF USING THE SAME

[75] Inventors: Jerry R. McGhee, Birmingham, Ala.; Milton E. Schaefer, Pasadena, Calif.

[73] Assignee: University of Alabama in Birmingham, Birmingham, Ala.

[21] Appl. No.: 738,042

[22] Filed: Nov. 2, 1976

[51] Int. Cl.² ............................................. A61B 10/00
[52] U.S. Cl. ...................................... 128/2 F; 128/300
[58] Field of Search ............... 128/2 F, 275, 295, 281, 128/282, 300, 301, 276; 248/363, 206 R

[56] References Cited

U.S. PATENT DOCUMENTS

| 296,609 | 4/1884 | Patee | 128/282 |
|---|---|---|---|
| 3,613,122 | 10/1971 | Gross et al. | 128/295 X |
| 3,662,928 | 5/1972 | Pogorski et al. | 222/211 |
| 3,890,204 | 6/1975 | Avery | 128/2 W X |
| 3,900,019 | 8/1975 | Logiadis | 128/2 F |

FOREIGN PATENT DOCUMENTS 189,341  5/1956  Fed. Rep. of Germany .......... 128/282

OTHER PUBLICATIONS

Carlson et al., *Am. J. Physiol.* 26: 169–177, 1910.
Lashly, K. S., *J. Exp. Psychol.* 1: 461–493, 1916.
Krasnogorsky, *Inn Med. V. Kinderh* 39: 613–730, 1931.
Curby, W. A., "Device for Collection of Human Parotid Saliva", *J. Lab. Clin. Med.* 41: 493–496, 1953.

*Primary Examiner*—Robert W. Michell
*Assistant Examiner*—Michael H. Thaler
*Attorney, Agent, or Firm*—Ferris M. Stout

[57] ABSTRACT

A saucer-shaped, resilient cup, sealed to a flat cover with an aperture in it to fit over the orifice of Stenson's duct from the parotid gland, adheres to the inside of the cheek, held in place by negative pressure, to collect the secretion of the parotid gland. Nothing protrudes from the mouth during collection of the sample.

3 Claims, 3 Drawing Figures

INTRAORAL CUP FOR COLLECTING SALIVA AND METHOD OF USING THE SAME

BACKGROUND OF THE INVENTION

The United States Government is entitled to a royalty-free, non-exclusive, non-transferable license to these patent rights by reason of research support by the National Institute for Dental Research.

The Intraoral Cup is in the field of diagnostic fluid collectors.

About 50 percent of saliva is produced by the parotid glands, the secretions of which reach the mouth through Stenson's ducts, which terminate in easily visible orifices on the inside of the cheek. Parotid secretion is quite similar, chemically, to tears. In common with other secretions, such as tears, milk, gut and lung secretions, saliva is a complex mixture of numerous types of proteins including enzymes, secretory immunoglobulins, and proteins such as lysozyme, lactoferrin and peroxidase. The immune processes of the circulating system, particularly lymphocytes and components of blood plasma, defend against microorganisms which attack through the circulatory system. Similarly immune processes in the secretory system defend our mucosal tissues from invading microorganisms. Just as analysis of immune reactions in the blood yields information about abnormalities within reach of circulating blood, so analysis of secretions can reveal much about the immune potential of this system.

Dental researchers have long been interested in the analysis of saliva, hoping to understand the role played by its constituents in controlling the organisms which cause dental caries and peridontal disease. In recent years, as automated clinical analysis of body fluids (particularly blood and urine) has become routine, biochemists have become interested in analysing the components of the secretory system. Such analysis can yield much information about the body's state of mobilization against specific pathogens. It can also illuminate biological processes such as drug metabolism and electrolyte balance.

Saliva in the mouth is contaminated with bacteria, food detritus, and sloughed-off epithelial cells. What has been long sought for by dental researchers, and more recently by clinical biochemists and immunologists, is a convenient way to non-invasively collect a sample of pure saliva as it is secreted by the glands which produce it. The most convenient source of such a sample is the parotid gland, which secretes about half of the saliva through Stenson's duct. Stenson's duct empties into the buccal cavity on the inside of the cheek. The secretion of the parotid gland from a given subject, as it comes from Stenson's duct, is a water-clear, nearly sterile fluid of consistent composition.

THE PRIOR ART

A device for collecting parotid saliva was first proposed over 65 years ago. Despite subsequent modifications, the basic concept has remained unchanged throughout the years to the present. The basic concept comprises a collector for parotid secretion connected by a tube to an extra-oral receptacle, and means for generating suction to hold the collector in place, the suction means also connected via tubing to an extra-oral source of mild suction, such as a rubber bulb.

In their original paper, Carlson and Crittenden[1] described a metal cup that was placed over the orifice of Stenson's duct and was held there by negative pressure, exerted by an external bulb, in an outer metal cup. Lashly[2] simplified this model by designing a single cup with two concentric chambers, the inner chamber for saliva collection and the outer for suction. Krasnogorsky[3] modified the outer cup ring and used silver tubing. Curby's[4] use of plastic cups and tubing introduced a major modification. In later studies one of the two tubes was replaced by a membrane on the outer ring for applying holding suction; however the saliva was still collected by external tubing. Numerous other investigators have used similar tubed cups in their studies with human parotid secretion.

[1] Carlson, A. J. and Crittenden, A. L.: The Relation of Ptyalin Concentration to the Diet and to the Rate of Secretion of the Saliva, *Am. J. Physiol.* 26:169–177, 1910
[2] Lashly, K. S.: Reflex Secretion of the Human Parotid Gland, *J. Exp. Psychol.* 1:461–493, 1916.
[3] Krasnogorsky, N. I.: Bedingte und Unbedingte Reflexium Kindesacter und ihre Bedeutung fur Dielinik, Ergebn d *Inn Med U Kinderh* 39:613–730, 1931.
[4] Curby, W. A.: Device for Collection of Human Parotid Saliva, *J. Lab. Clin. Med.* 41:493–496, 1953.

Saliva-collecting cups with tubes which lead out of the mouth have several drawbacks. The presence of the tube, or tubes, makes it difficult to maintain the suction necessary to hold the cup in place over Stenson's duct. With some people, the time necessary to collect a useful sample may be 10 or 15 minutes or longer. Any motion of the subject, his lips, tongue, cheeks, or mouth, is likely to cause leakage if the tube is disturbed. Moreover the tubing itself represents a large dead volume which must be filled with saliva before useful collection can begin. It is difficult to sterilize fine tubing and the connecting joints of the tubing to the cup itself. Finally the device, including its sterile tubing, is usually too expensive to make possible a saliva collector which can be thrown away after use. There exists therefore a need for a simple, disposable, and effective device which can be used to collect uncontaminated parotid saliva samples without causing discomfort to subjects even for the relatively long times required by slow saliva producers.

SUMMARY OF THE INVENTION

One object of the invention is to provide means for collecting samples of saliva which means are entirely contained within the mouth during the collection process.

Another object of the invention is to provide a device for collecting saliva which can be readily sterilized.

Yet another object of the invention is to provide a saliva-collecting device which is simple and economical of manufacture, so that the device can be discarded after use.

Still another object of the invention is to provide a device for collecting saliva secreted by the parotid glands, which when put in place over Stenson's duct, will not easily become dislodged by movement of the subject's mouth while the sample is collecting in the device.

Yet a further object of the invention is to provide means for collecting a sample of the secretion of the parotid gland which means can be easily utilized by para-professional personnel.

These objects, and others which will be made clear in the subsequent description of the invention, are achieved by providing a saucer-shaped device made of resilient material, having a flat and convex side. The flat side of the cup has an aperture in it which fits over Stenson's duct. In use, the cup is held against the side of the cheek by slight negative pressure created when the convex side of the cup is compressed, and, by reason of its elasticity, tends to resume its non-compressed shape. Saliva collects in the portion of the cup below the aperture. The subject may talk and move about at will while saliva is being collected. Once the cup is in place, it is quite comfortable for the subject, a quality of particular importance with little children. When a sufficient sample of saliva has been collected, the cup is released by breaking the suction holding the cup against the cheek. The cup is withdrawn from the mouth, and set upon its convex side, so that the sampled saliva can be pipetted into a suitable container for analysis.

THE DRAWINGS

THE PREFERRED EMBODIMENTS:

The following description of preferred embodiments are illustrative of the invention and are not to be construed as limiting it.

Figure 1:
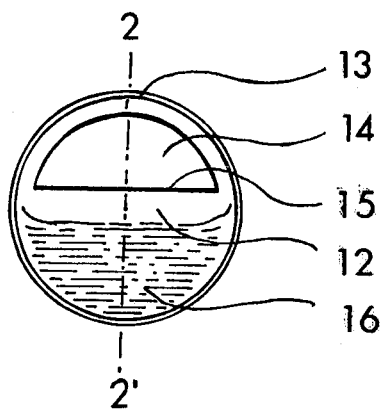
FIG. 1 is a plan view of the Intraoral Cup as seen from the flat side.
Figure 2:
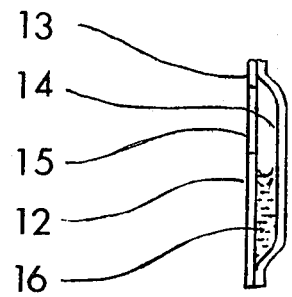
FIG. 2 is an edge-wise sectional view of the cup taken through the line 2 — 2' of FIG. 1.

Referring to the drawings, FIG. 1 shows a plan view of the cup. Flat side 12 is sealed around its periphery 13 to the convex side 14, part of which is shown through aperture 15. Aperture 15 may be of any convenient shape. It must be large enough to enable easy placement over Stenson's duct, yet not so large as to allow enough cheek to bulge into the cup to relieve the negative pressure which holds the cup in place, or to severely limit the volume of reservoir 16. Aperture 15 must be positioned on the flat side 12 so that a reservoir 16 for the collection of saliva beneath it is created.

We have found that a round shape for the cup works well, with the aperture 15 defined by a flat lower edge about one third of a diameter below the periphery and an upper edge concentric with the periphery.

All edges of the cup must be smooth, particularly the edges of the aperture, to prevent leakage of air into the cup, and loss of the negative pressure which holds it in place.

The dimensions of the cup must be such as to allow a comfortable fit in the mouth, and at the same time allow sufficient volume for the reservoir. We have found that a depth of about ¼ of an inch between the flat side 12 and the convex side 14 allows ready collection of samples of about 2 milliliters depending on the diameter used. We have found that a selection of four diameters for the cup, of ⅞ inch, 1 inch, 1⅛ inch, and 1¼ inch, is sufficient for sampling saliva in most people's mouths, including small children's mouths.

The cup may be made of any material which posesses the necessary elasticity, which can be sterilized, and which is compatible with the oral environment. In one embodiment, the cup is made of thin stainless steel. Such cups can be readily sterilized in an autoclave, and thus can be many times reused.

In another embodiment, the cup is made of transparent plastic, such as 0.020 inch Mylar TM film. The transparency of the plastic allows ready positioning of the cup, since the orifice of Stenson's duct can be readily seen, in good light, through the cup as it is put in place. Moreover, the rate with which saliva is produced can be visually monitored. Cups made of transparent plastic can be packaged in sterilizing envelopes and sterilized with ethylene oxide. They are cheap enough to be discarded after use. In yet another embodiment the cup can be made with a serial number impressed upon the flat side. The cup can be made with an etched area for receiving identifying indicia.

Figure 3:
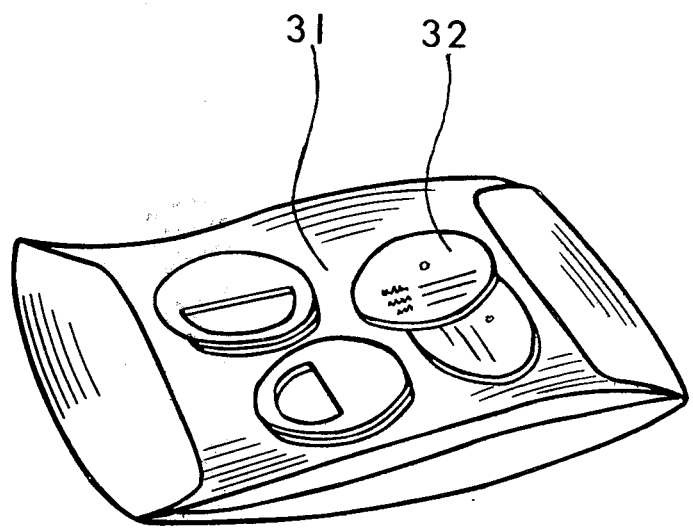
FIG. 3 is a plan view of a packaged kit for collecting saliva samples.

In our preferred embodiment, the cup, made of 0.020 inch Mylar TM film, is packaged in pairs in sterilizing envelopes as shown in FIG. 3, at 31. Self-adhering, sterilizable labels 32, cut so as to fit over the aperture and seal to the flat side of the cup are packaged in the same envelopes. Indicia are provided on the non-adhering side of the labels for patient identification and the like. This embodiment enables medical personnel to identify each cup (for example when many patients are sampled) and to seal each cup with the label, thereby reducing the risk of contamination and evaporation, and at the same time preparing the cups for transportation, refrigeration, or storage. To transfer saliva from the cup to a test vessel, it is only necessary to pierce the label with a syringe and withdraw the sample from the cup.

Use of the Intraoral Cup

A parotid saliva collection is made with the cup by selecting the largest cup that will fit in the buccal vestibule comfortably. The cup is held between the thumb and forefinger of one hand with the flat surface of the cup toward the cheek surface where it is to be placed. The aperture is oriented so that its straight edge is parallel to the floor of the mouth and the aperture is in the superior position. This ensures sufficient space in the reservior to collect saliva. The forefinger of the other hand is used to gently retract the corner of the mouth on the side to be sampled, and the cup is slid into the cheek with the round side next to the teeth and the aperture in the flat side covering Stenson's duct of the parotid gland. Usually the proper sized cup will automatically cause the aperture to fall right over the duct orifice. It is a simple matter to check the position of the cup, since the orifice can be easily seen through the clear plastic cup, with good light. Gentle pressure on the outside of the cheek over the cup will express a small amount of air, creating a slight negative pressure which helps to hold the cup in place.

Collection of sample can be timed, or a visual inspection can be made to determine when enough saliva for laboratory assay has accumulated in the cup.

Removal of the cup with the sample collected is a reverse procedure to that of placement. The corner of the mouth is gently retracted with the forefinger of one hand and the thumb and forefinger of the other hand is used to carefully grasp the forward edge of the cup. The cup is pulled out of the mouth, keeping it in the same relative position it had in the mouth, that is, upright, with the flat edge of the aperture parallel to the floor. When clear of the lips, the cup is turned with its round side down. In this position the contents will not spill, and the cup may be set down while the second cup (if used) is removed. A self-adhering label is marked to identify each cup and put in place over the aperture. The cups are refrigerated until it is convenient to transfer their contents, with a hypodermic syringe, to a vessel for assay.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A method for collecting the secretion of the parotid gland which comprises the steps of
    inserting in the mouth, against the side of the cheek, an intraoral cup which has a flat side with an aperture in it and a resilient, convex side,
    positioning the intraoral cup so that the aperture in the flat side fits over the orifice of Swenson's duct,
    inducing negative pressure within the cup sufficient to hold it in place while parotid secretion collects in it, by compressing the convex side of the cup inwardly, and then releasing it, and
    removing the cup when a sufficient sample of parotid secretion has collected in it.

2. An intraoral cup for collecting the secretion of the parotid gland which comprises
    a flat side having an aperture in it substantially offset from its center and
    a saucer shaped resilient side without an orifice, sealed on its periphery to the periphery of the flat side, its resilence providing means for sustaining negative pressure within the cup when the cup is placed against the inside of a subject's cheek with the aperture over Stenson's duct and the cup is compressed momentarily and released, said cup being of a size to fit comfortably inside a person's cheek.

3. The intraoral cup of claim 2 made of transparent, resilient plastic.

* * * * *